(12) United States Patent
Goncharuk et al.

(10) Patent No.: US 12,270,649 B2
(45) Date of Patent: Apr. 8, 2025

(54) GEOCHEMICAL ANALYSIS OF DRAINAGE BASINS

(71) Applicant: X Development LLC, Mountain View, CA (US)

(72) Inventors: Artem Goncharuk, Mountain View, CA (US); Kevin Forsythe Smith, Pleasanton, CA (US); Alex S. Miller, Cambridge, MA (US)

(73) Assignee: X Development LLC, Mountain View, CA (US)

( * ) Notice: Subject to any disclaimer, the term of this patent is extended or adjusted under 35 U.S.C. 154(b) by 0 days.

(21) Appl. No.: 18/726,318

(22) PCT Filed: Mar. 29, 2024

(86) PCT No.: PCT/US2024/022167
§ 371 (c)(1),
(2) Date: Jul. 2, 2024

(87) PCT Pub. No.: WO2024/206773
PCT Pub. Date: Oct. 3, 2024

(65) Prior Publication Data
US 2024/0426609 A1 Dec. 26, 2024

Related U.S. Application Data

(60) Provisional application No. 63/493,538, filed on Mar. 31, 2023.

(51) Int. Cl.
*G01C 13/00* (2006.01)
*G01N 21/31* (2006.01)
(Continued)

(52) U.S. Cl.
CPC .............. *G01C 13/00* (2013.01); *G01N 21/31* (2013.01); *G01N 33/18* (2013.01); *G01V 1/306* (2013.01); *G01V 20/00* (2024.01)

(58) Field of Classification Search
USPC ............................................................ 702/2
See application file for complete search history.

(56) References Cited

U.S. PATENT DOCUMENTS 5,388,456 A 2/1995 Kettel
9,891,331 B2 2/2018 Hornbostel et al.
(Continued)

OTHER PUBLICATIONS

Abdelal et al., "Wireless Sensor Networks for Hydrological Monitoring, Helpful Tools for Accurate Models," Water Resources Management and Sustainability, Mar. 16, 2023, pp. 3-14.
(Continued)

*Primary Examiner* — Paul D Lee
(74) *Attorney, Agent, or Firm* — Fish & Richardson P.C.

(57) ABSTRACT

Techniques for determining a mineralogy of a portion of a drainage basin include identifying topography data associated with a drainage basin comprising at least one body of water; identifying weather data associated with the drainage basin; identifying first sensor data associated with a first water sensor installed in the drainage basin; identifying second sensor data associated with a second water sensor that is located downstream of the first water sensor in the drainage basin; providing the first sensor data, second sensor data, topography data, and weather data as input to a machine learning algorithm; and determining, by the machine learning algorithm, a mineralogy of a portion of the drainage basin.

36 Claims, 4 Drawing Sheets

(51) Int. Cl.
   *G01N 33/18* (2006.01)
   *G01V 1/30* (2006.01)
   *G01V 20/00* (2024.01)

(56) References Cited

U.S. PATENT DOCUMENTS

2015/0347647 A1* 12/2015 Osborne .............. B09C 1/002
                                                    703/6
2020/0184214 A1   6/2020 Casas et al.
2021/0318465 A1  10/2021 Prindle et al.
2021/0365808 A1* 11/2021 Davies ................. E21B 41/00

OTHER PUBLICATIONS

Bi et al., "Multi-indicator water quality prediction with attention-assisted bidirectional LSTM and encoder-decoder," Information Sciences, May 2023, 625:65-80.

International Search Report and Written Opinion in International Appln. No. PCT/US2024/022167, dated Jun. 25, 2024, 16 pages.

Rodriguez-Galiano et al., "Machine learning predictive models for mineral prospectivity: An evaluation of neural networks, random forest, regression trees and support vector machines," Ore Geology Reviews, Dec. 2015, 71:804-818.

Shirmard et al., "A review of machine learning in processing remote sensing data for mineral exploration," Remote Sensing of Environment, Jan. 1, 2022, 268:112750.

Vogeti et al., "Deep learning algorithms and their fuzzy extensions for streamflow prediction in climate change framework," Journal of Water and Climate Change, Feb. 10, 2024, 15 (2):832-848.

Zhang et al., "A Machine Learning Approach for Prediction of the Quantity of Mine Waste Rock Drainage in Areas with Spring Freshet," Minerals, Mar. 8, 2023, 13(3):376.

Palmer, "The Geochemical Interpretation of Water Analyses," Department of the Interior United States Geological Survey, 1911, 479:35 pages.

\* cited by examiner

GEOCHEMICAL ANALYSIS OF DRAINAGE BASINS

CROSS-REFERENCE TO RELATED APPLICATIONS

This application is a National Stage Application under 35 U.S.C. § 371 and claims the benefit of International Patent Application No. PCT/US2024/022167, filed on Mar. 29, 2024, which claims priority to U.S. Provisional Patent Application Ser. No. 63/493,538, filed Mar. 31, 2023, the disclosure of which is incorporated herein by reference in its entirety.

TECHNICAL FIELD

This disclosure generally relates to performing geochemical analysis of a drainage basin to identify upstream mineralogy.

BACKGROUND

Subsurface exploration can be performed using many techniques. Many applications involve directly recording seismic or acoustic energy in the subsurface. However, precision sensing in other fields has enabled other means of measuring subsurface mineralogy and other subsurface parameters.

SUMMARY

In general, the disclosure involves systems, apparatus, and computer-implemented methods for determining a mineralogy of a portion of a drainage basin. For example, a system of one or more computers can be configured to perform particular actions by virtue of having software, firmware, hardware, or a combination of them installed on the system that in operation causes or cause the system to perform the actions. One or more computer programs can be configured to perform particular actions by virtue of including instructions that, when executed by data processing apparatus, cause the apparatus to perform the actions.

In an example implementation, a computer-implemented method for determining a mineralogy of a portion of a drainage basin includes identifying, by one or more hardware processors, topography data associated with a drainage basin comprising at least one body of water; identifying, by the one or more hardware processors, weather data associated with the drainage basin; identifying, by the one or more hardware processors, first sensor data associated with a first water sensor installed in the drainage basin; identifying, by the one or more hardware processors, second sensor data associated with a second water sensor, the second water sensor located downstream of the first water sensor in the drainage basin; providing the first sensor data, second sensor data, topography data, and weather data as input to a machine learning algorithm; and determining, by the machine learning algorithm, a mineralogy of a portion of the drainage basin.

In an aspect combinable with the example implementation, the topography data comprises at least one of elevation data or slope data within the drainage basin.

In another aspect combinable with one, some, or all of the previous aspects, the weather data comprises at least one of temperature data, precipitation data, or wind data for a time period.

In another aspect combinable with one, some, or all of the previous aspects, the time period is a least one month in duration.

In another aspect combinable with one, some, or all of the previous aspects, the first water sensor and the second water sensor are configured to measure a conductivity of the water.

In another aspect combinable with one, some, or all of the previous aspects, the first water sensor and the second water sensor are configured to measure at least one of: a mineral composition of the water; a flowrate of the water; a pH of the water; or a temperature of the water.

Another aspect combinable with one, some, or all of the previous aspects includes identifying, by the one or more hardware processors, remote sensing data associated with the drainage basin; and providing, by the one or more hardware processors, the remote sensing data as additional input to the machine learning algorithm.

In another aspect combinable with one, some, or all of the previous aspects, the remote sensing data comprises at least one of satellite imaging or synthetic aperture radar imaging.

Another aspect combinable with one, some, or all of the previous aspects includes determining, by the machine learning algorithm, a recommended location for performing a hyperspectral scan in the drainage basin in response to determining the mineralogy of the portion of the drainage basin.

The disclosed solution is advantageous in that it permits discovery and analysis of upstream regions of a drainage basin without necessarily performing costly and time consuming surveys of each individual region. By harnessing readily available regional data with a relatively inexpensive sensor array in a river, detailed analysis and exploration is possible.

The details of one or more implementations of the subject matter of this specification are set forth in the accompanying drawings and the description below. Other features, aspects, and advantages of the subject matter will become apparent from the description, the drawings, and the claims.

DESCRIPTION OF DRAWINGS

This disclosure relates to performing geochemical analysis of a water basin to identify upstream mineralogy.

DETAILED DESCRIPTION

This disclosure describes a system and method for performing an analysis (e.g., chemical, electrochemical) of water in a drainage basin, such as a region of land where surface water converges to a single river and flows into another body of water, in light of external environmental occurrences to identify upstream mineralogy of the drainage basin. For example, following a precipitation event in a particular region of the drainage basin, an increased concentration of copper sulfates in the mouth of the basin can indicate that there is a copper deposit upstream in the region that experienced a precipitation and or erosional event. Different environmental events (e.g., precipitation or erosion) can have an outsized effect on a particular region of a drainage basin, or a particular hydrology or mineralogy of that region. For example, regions of the drainage basin that accumulate snow will have detectable seasonal runoff patterns within the drainage basin. In another example, if a precipitation event is light or slow, then there will likely be less runoff associated with that event than a heavy or sudden torrential rain. Measuring groundwater models or hydrology models, as well as detailed weather data can be used to predict or anticipate likely regions of the drainage basin that will affect water sensors within the river system. By establishing a network of sensors throughout a drainage basin or river system, and analyzing with weather, hydrology and other additional data, inferences can be made regarding the properties of the drainage basin.

Figure 1:
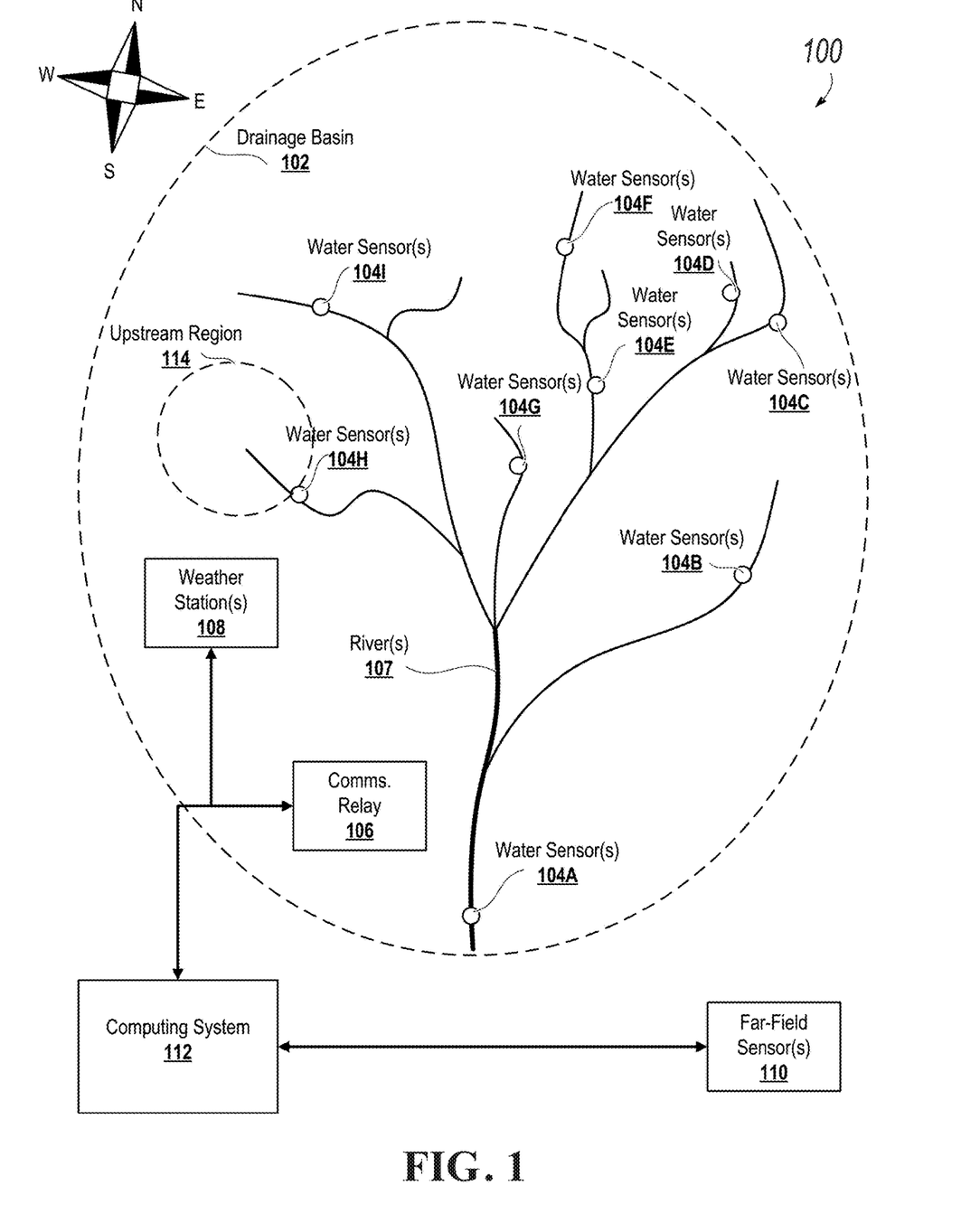
FIG. 1 illustrates an example system for analyzing upstream mineralogy in a drainage basin.

FIG. 1 illustrates an example system 100 for determining mineralogy of one or more upstream regions of a drainage basin 102. Drainage basin can include one or more rivers 107 which join together at a root to form a hierarchical structure. An array of water sensors 104A-104I can be deployed throughout the river to measure chemical and physical properties of the water flowing down the river. Additional sensors, including one or more weather stations 108 (e.g., including, in some aspects, weather radars) and far-field sensors 110 provide additional data. A computing system 112 receives all of the sensed data and determines one or more insights from the data related to the mineralogy upstream, for example, related to the mineralogy of upstream region 114.

Water sensors 104A-104I can be placed throughout the river and its supplying streams and tributaries. In example implementations, water sensors 104A-104I are fixed sensors that are deployed permanently or semi-permanently within the river. In example implementations, water sensors 104A-104I are released into the river, and flow downriver with the current to a collection point, where they are collected and their data is retrieved. In example implementations, the water sensors 104A-104I are disposable, and transmit their data before naturally degrading within the water. In implementations where water sensors 104A-104I flow with the river, they can receive location data, e.g., using GPS signals, or ground station signals. For example, one or more of the water sensors 104A-104I can include a GPS/GNSS radio. In example implementations, the water sensors 104A-104I estimate their location based on a known release point, time, measured accelerations, and a physics model of the river.

The water sensors 104A-I can measure many parameters associated with the water including temperature, flow rate, level, conductivity, pH, salt concentration, other ion concentrations (e.g., sulfite concentration), clarity, purity, or other parameters. Having an array of sensors arranged throughout the river 107 enables localization of source materials affecting the concentration of minerals in downstream regions. For example, sensor 104A measures a mixture of all of the supplying tributaries, while water sensor 104E only measures a few particular streams/tributaries. In example implementations, these water sensors 104A-104I are deployed continuously, or near continuously for at least one season, or one year (or other time duration), to accumulate sufficient data in order to compensate for normal seasonal variation.

Weather station 108 can be a single weather station, or multiple distributed weather stations throughout drainage basin 102. In general, weather station 108 records weather events and conditions throughout drainage basin 102 including precipitation, humidity, temperature, wind intensity, wind direction, and other things. In example implementations, weather station(s) 108 records weather and stores it, periodically transmitting or sending the information to computing system 112. In example implementations, the weather station(s) 108 perform local processing, and provide computing system 112 with processed weather data, such as estimated total rainfall, or filtered and/or denoised wind data.

In example implementations, a communications relay 106 is provided, which can receive data from the relatively low power water sensors 104A-I and relay the data to computing system 112. In example implementations, the communications relay 106 performs additional data processing such as filtering, aggregating, denoising, or other processes to raw data, or processed data received from one or more sensors. In example implementations, the water sensors 104A-I communicate directly with the computing system 112, and no communications relay 106 is necessary.

Far-field sensors 110 can include satellites or aircraft borne sensors, as well as other long range sensors such as seismometers. Far-field sensors 110 can provide data representing a number of related or environmental parameters such as vegetation cover, ground type, river erosion rate, river location/geometry, water depth, cloud cover, solar irradiation, magnetic permeability, seismic activity, or others. Far-field sensors 110 can be, for example, satellites or aircraft (including unmanned aircraft) providing color or infrared images, synthetic aperture radar images, or hyperspectral scans. Far-field sensors 110 can additionally include seismometers, magnetometers, electromagnetic and magnetic surveys, accelerometers, or other sensors for detecting subsurface acoustic energy. Far-field sensors 110 can communicate with computing system 112 either directly, or via communications relay 106, and can send raw or processed data to computing system 112 for analysis.

In one example, following a heavy rainstorm detected in the western region of the drainage basin, weather station 108 could record the rain event. As time passes, and flow rate through portions of river 107 increases due to the rain, this can be detected by water sensors 104H and 104A. A change in mineral composition in addition with the change in flow rate of the river 107, viewed in light of the known rain storm, and for example, vegetation cover data from far-field sensors 110, can be correlated by computing system 112 with a likely mineral deposit in upstream region 114.

Figure 2:
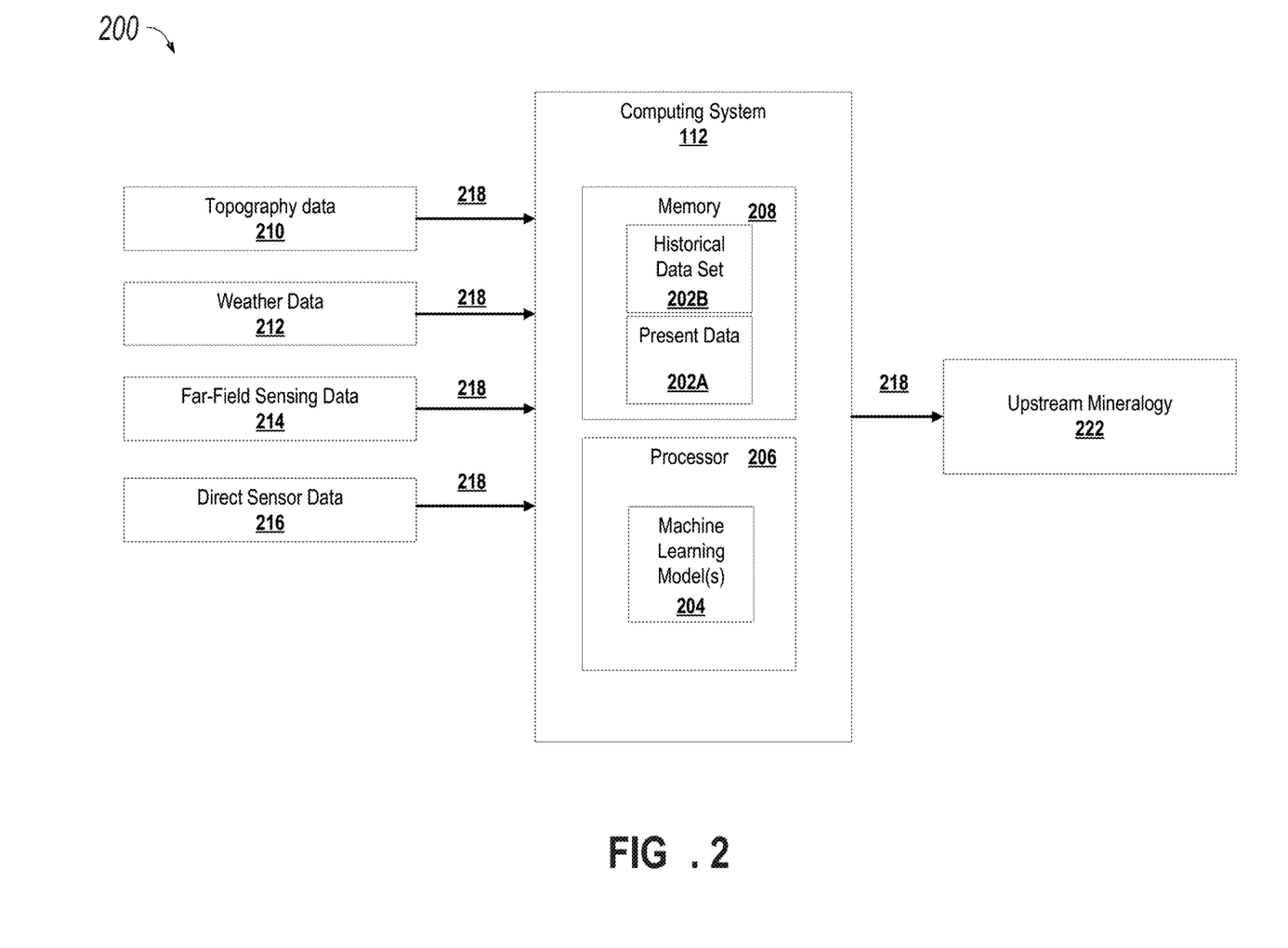
FIG. 2 is a schematic diagram of a computing system with a machine learning algorithm for determining upstream mineralogy of a drainage basin.

FIG. 2 is a schematic diagram of a system 200 with a machine learning algorithm for analyzing upstream mineralogy in a drainage basin. The computing system 112 can receive data from various systems (e.g., the communications relay 106 of FIG. 1) via a communications link 218. The communication link 218 can be but is not limited to a wired communication interface (e.g., USB, Ethernet, fiber optic) or wireless communication interface (e.g., Bluetooth, ZigBee, Wi-Fi, infrared (IR), CDMA2000, etc.). The communication link 218 can be used to communicate directly or indirectly, e.g., through a network, with the computing system 112.

The computing system 112 receives present data 202A from various sources via the communications link 218. Present data 202A can be data included in the most recent readings taken from water sensors 104A-I, weather station (s) 108, or other sensors. Present data 202A can include, but is not limited to topography data 210, which can include survey data or a three dimensional model of a geographic region, weather data 212, far-field sensing data 214, and direct sensor data 216 which can include other data sources or devices being used in conjunction with the systems described herein. In example implementations, the present data 202A can be received in real-time or near real-time.

Real-time can mean within seconds, or minutes, or with no intentional delay between collection of data and receipt of data. In example implementations, the present data 202A includes predicted or inferred data that is not directly measured but can be based on forecasted data. For example, present data 202A can include weather forecast data for the next 10 days. The present data 202A is then used by the machine learning model 204 operating with a processor 206 to generate a quantified output.

Topography data 210 can include map data of one or more drainage basins, including elevation data and slope data for the drainage basin. In example implementations, topography data 210 includes seasonal data, or historical data that can be used to estimate variances in the river or drainage basin from year to year or season to season. In example implementations, topography data 210 includes depth data associated with the river and can be used to generate a physics model of the river representing flow rate, flow amount, erosion rates, and other physical parameters associated with water flow in the river. In example implementations, topography data 210 includes one or more groundwater models, which represent the hydrology of the region, and how water moves through the subsurface. In example implementations, topography data 210 includes vegetation data describing type and quantity of vegetation within the drainage basin. This vegetation data can be used to estimate erosion, and mineralogy of various regions within the drainage basin. In example implementations, the topography data 210 includes rock types such as sedimentary, igneous, or metamorphic rock, for regions of the drainage basin. In example implementations, the topography data 210 includes various other parameters associated with the surface and subsurface of the drainage basin being analyzed.

Weather data 212 includes recent weather patterns and information such as temperature, precipitation including type and amount, wind speed and direction, atmospheric humidity, visibility, cloud cover including amount and type, pollution or concentrations of other gasses, and other weather parameters such as atmospheric pressure. Weather data 212 can include current or recent data, as well as historical data, trends, and averages. Weather data 212 can further include future, or predicted data, such as the expected temperatures or precipitation for some future period of time (e.g., 7 days, 1 month etc.). In example implementations, weather data 212 can be specific to a region containing the drainage basin, or a particular portion of the drainage basin. In example implementations, weather (or weather and atmospheric) data 212 includes neighboring regions, or is global (e.g., worldwide) weather data. Weather data 212 can be collected by a number of sources, including local weather stations, satellite or remote weather sensors, meteorological forecasts, meteorological historical data, and others.

Far-field sensing data 214 includes imaging data and other sensing that occurs at a distance or over a large region associated with the drainage basin. This can include imaging from aircraft or satellites, such as color imaging, infrared imaging, ultraviolet imaging, hyperspectral scans, radio or radar imaging, such as synthetic aperture radar, among other images. In example implementations, far-field sensing data 214 includes additional sensed data, such as seismic data recorded by one or more seismometers, fiber optic sensing, or accelerometers. In example implementations, far-field sensing data 214 includes geomagnetic data, for example, captured by an overflying aircraft.

Direct sensor data 216 includes data recorded by water sensors within a river of the drainage basin. The water sensors can be arranged in an array or distributed throughout the river and its supplying tributaries. In example implementations, the direct sensor data 216 includes data from one or both of permanent or semi-permanent water sensors, as well as disposable or mobile sensors configured to drift down the river. In example implementations, direct sensor data 216 includes measurements of water pH, ORP, total dissolved solids (TDS), turbidity, conductivity, hardness (or concentration dissolved calcium and magnesium), total organic carbon (TOC), nitrate and/or nitrite concentrations, phosphate, heavy metal concentrations, microbial concentrations, or other parameters such as particular ions and mineral concentrations. In example implementations, direct sensor data 216 further includes river parameters such as depth, flow rate, water temperature, or flow directions.

The computing system 112 can store a historical data set 202B in memory 208. The historical data set can include all data that has previously been used in a particular region, or a subset of the previous data. The historical data set 202B can also include data relating to common trends seen across multiple regions or locations, or trends seen among particular locations or regions or any suitable combination thereof.

The machine learning model 204 receives the present data 202A, and the historical data set 202B and generates a quantified output such as upstream mineralogy 222. For example, the machine learning model 204 can generate a model representing the probability of an iron deposit in various upstream regions of the drainage basin. In example implementations the machine learning model 204 can generate an estimate of carbon transfer by the river, or an estimated erosion rate including future erosion paths. In example implementations, the machine learning model can identify patterns that indicate a rate of change (increase or decrease) of a mineral or chemical that would indicate the presence and potential exposure of earth resources of interest and identify potential locations. In example implementations, upstream mineralogy 222 can include a measure of mineralized carbon and carbon transit (e.g., capture and release) throughout the drainage basin.

In example implementations, the machine learning model 204 is a deep learning model that employs multiple layers of models to generate an output for a received input. A deep neural network is a deep machine learning model that includes an output layer and one or more hidden layers that each apply a non-linear transformation to a received input to generate an output. In some cases, the neural network may be a recurrent neural network. A recurrent neural network is a neural network that receives an input sequence and generates an output sequence from the input sequence.

In particular, a recurrent neural network uses some or all of the internal state of the network after processing a previous input in the input sequence to generate an output from the current input in the input sequence. In some other implementations, the machine learning model 204 is a convolutional neural network. In example implementations, the machine learning model 204 is an ensemble of models that may include all or a subset of the architectures described above.

In example implementations, the machine learning model 204 can be a feedforward auto-encoder neural network. For example, the machine learning model 204 can be a multi-layer auto-encoder neural network. The machine learning model 204 may include an input layer, one or more hidden layers, and an output layer. In example implementations, the neural network has no recurrent connections between layers. Each layer of the neural network may be fully connected to the next, e.g., there may be no pruning between the layers.

The neural network may include an optimizer for training the network and computing updated layer weights, such as, but not limited to, ADAM, Adagrad, Adadelta, RMSprop, Stochastic Gradient Descent (SGD), or SGD with momentum. In example implementations, the neural network may apply a mathematical transformation, e.g., a convolutional transformation or factor analysis to input data prior to feeding the input data to the network.

In example implementations, the machine learning model 204 can be a supervised model. For example, for each input provided to the model during training, the machine learning model 204 can be instructed as to what the correct output should be. The machine learning model 204 can use batch training, e.g., training on a subset of examples before each adjustment, instead of the entire available set of examples. This may improve the efficiency of training the model and may improve the generalizability of the model. The machine learning model 204 may use folded cross-validation. For example, some fraction (e.g., the "fold") of the data available for training can be left out of training and used in a later testing phase to confirm how well the model generalizes. In example implementations, the machine learning model 204 may be an unsupervised model. For example, the model may adjust itself based on mathematical distances between examples rather than based on feedback on its performance.

The machine learning model 204 can be, for example, a deep-learning neural network or a "very" deep learning neural network. For example, the machine learning model 204 can be a convolutional neural network. The machine learning model 204 can be a recurrent network. The machine learning model 204 can have residual connections or dense connections. The machine learning model 204 can be an ensemble of all or a subset of these architectures. The model may be trained in a supervised or unsupervised manner. In some examples, the model may be trained in an adversarial manner. In some examples, the model may be trained using multiple objectives, loss functions or tasks.

In example implementations, the machine learning model 204 can generate upstream mineralogy 222 based on recorded data only. In other words, the upstream mineralogy 222 can be a new image, based on no prior collections. In example implementations, the machine learning model 204 can use input data (e.g., direct sensor data 216) to improve a previously existing mineralogy data or survey that was acquired by other means (e.g., ground penetrating radar, samples, etc.). For example, a gravimetric survey can be enriched to include increased information such as more temporal resolution, or more spatial resolution, based on topography data 210, weather/atmospheric data 212, and far-field sensing data 214, and direct sensor data 216 received at the machine learning model 204 in order to create upstream mineralogy 222.

In example implementations, the machine learning model 204 can provide suggested additional data that could further improve the output of the machine learning model 204. For example, the machine learning model 204 could provide analysis of the direct sensor data 216 and suggest additional sensor deployment locations, or times in order to further improve upstream mineralogy 222. In another example, the machine learning model 204 could provide recommended locations for future investigation using different far-field sensing.

Figure 3:
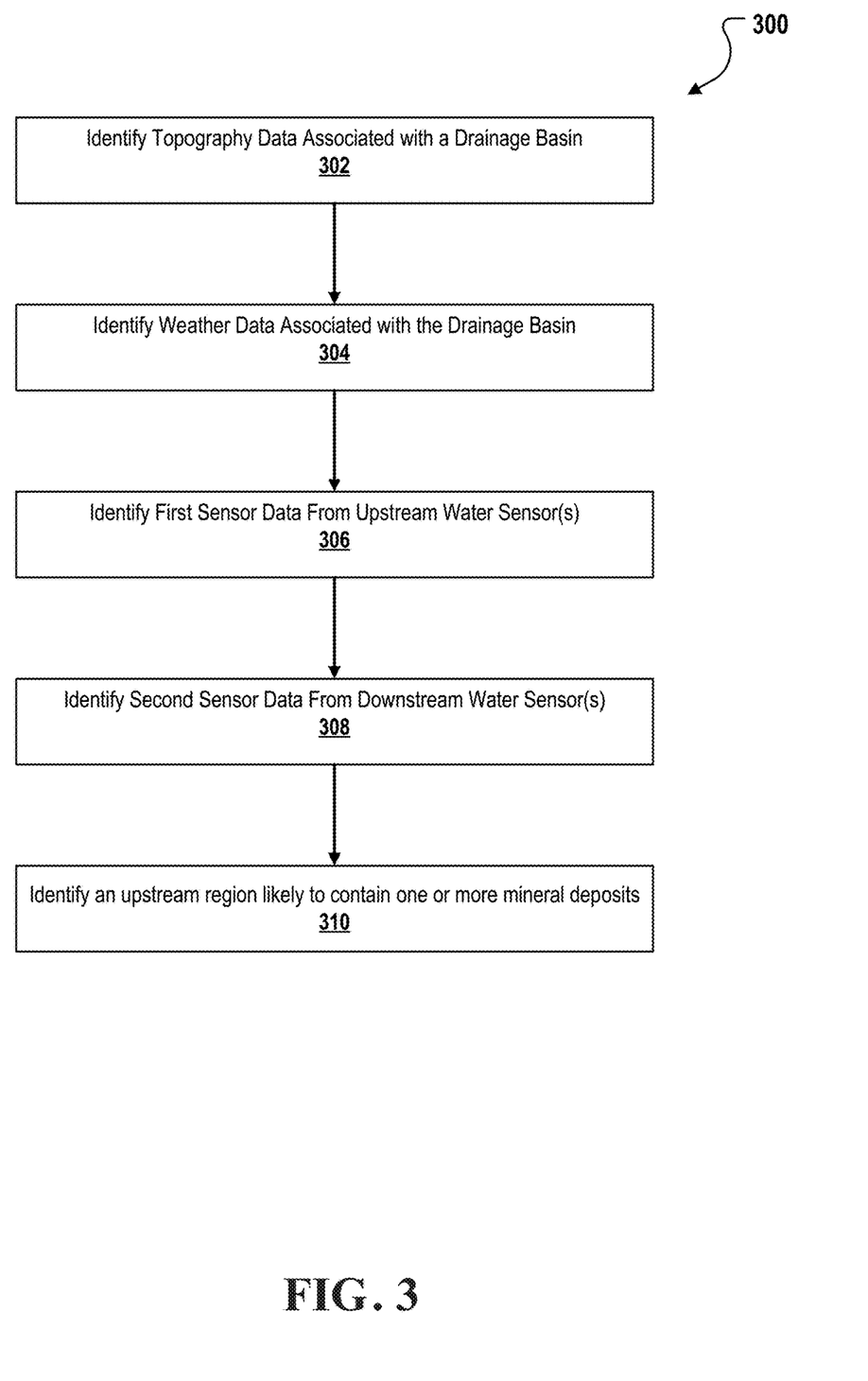
FIG. 3 is a flowchart depicting an example process for determining upstream mineralogy of a drainage basin.

FIG. 3 is a flowchart depicting an example process 300 for performing geochemical analysis of a water basin. It will be understood that process 300 may be performed, for example, by any suitable system, environment, software, and hardware, or a combination of systems, environments, software, and hardware as appropriate. In some instances, process 300 can be performed by the system 100, or portions thereof, described in FIG. 1, as well as other components or functionality described in other portions of this description. In other instances, process 300 may be performed by a plurality of connected components or systems. Any suitable system(s), architecture(s), or application(s) can be used to perform the illustrated operations.

At 302, topography data associated with a drainage basin is received. In example implementations the topography data is received periodically, e.g., annually, or monthly. Topography data can be gathered via remote sensing techniques, or from survey or cartographic data, among other sources. In example implementations, topography data includes elevation data and slope data for the drainage basin. In example implementations, topography data includes seasonal data, or historical data that can be used to estimate variances in the river or drainage basin from year to year or season to season. In example implementations, topography data includes depth data associated with the river, and can be used to generate a physics model of the river representing flow rate, flow amount, erosion rates, and other physical parameters associated with water flow in the river. In example implementations, topography data includes vegetation data describing type and quantity of vegetation within the drainage basin. This vegetation data can be used to estimate erosion, and mineralogy of various regions within the drainage basin. In example implementations, the topography data includes rock types such as sedimentary, igneous, or metamorphic rock, for regions of the drainage basin. In example implementations, the topography data includes various other parameters associated with the surface and subsurface of the drainage basin being analyzed. The topography data can be received by a computing system, or retrieved (e.g., via a web crawler) by the computing system and stored in a repository such as a hard drive. In example implementations several sets of topography data associated with the drainage basin is stored and associated with dates, which permits observation and time-change analysis of the topography of the region.

At 304, weather data associated with the drainage basin is received. Weather data can include recent weather patterns and information such as temperature, precipitation including type and amount, wind speed and direction, atmospheric humidity, visibility, cloud cover including amount and type, pollution or concentrations of other gasses, and other weather parameters such as atmospheric pressure. Weather data can include current or recent data, as well as historical data, trends, and averages. In example implementations, weather data can be specific to a region containing the drainage basin, or a particular portion of the drainage basin. In example implementations weather data includes neighboring regions, or is global (e.g., worldwide) weather data. Weather data can be collected by a number of sources, including local weather stations, satellite or remote weather sensors, meteorological forecasts, meteorological historical data, and others. In example implementations, the weather data is pulled from publicly available online sources such as windy.com or weather.com. In example implementations, this publicly available weather data can be combined with data collected from local sensors or meteorological stations within the drainage basin.

At 306, sensor data from one or more upstream water sensors is received. The sensor data can be received via a wireless link between the water sensors and a communications relay, or directly from the sensors. In example implementations, the sensor data includes measurements of water pH, total dissolved solids (TDS), turbidity, conductivity, hardness (or concentration dissolved calcium and magnesium), total organic carbon (TOC), nitrate and/or nitrite concentrations, heavy metal concentrations, microbial concentrations, or other parameters such as particular mineral concentrations. Sensor data from the upstream water sensors can also include other parameters such as flow rate, water temperature, water level, turbulence, or others. The upstream sensor data can represent water chemistry and content in one or more tributaries, streams, lakes, ponds, or supplying rivers that are upstream in the drainage basin.

At 308, sensor data from one or more downstream water sensors is received. The sensor data can be similar to the sensor data from the upstream sensors received at 306, except that it represents chemistry and content in at one or more downstream locations in the river system. In example implementations, an array of water sensors within the river system forms a hierarchical structure, with a root sensor being the most downstream sensor, and each upstream sensor representing one or more branching tributaries.

At 310, an upstream region likely to contain one or more deposits of interest, such as mineral deposits, is identified by providing the weather data, topography data, and the upstream and downstream sensor data to a machine learning model. The machine learning model can correlate data including recent erosion patterns, weather events, seismic events, and associated changes in chemical composition or water properties in different portions of the river to identify regions within the drainage basin that are likely to contain a particular mineral deposit. For example, an earthquake or other seismic event may release minerals in a particular portion of the river. The machine learning algorithm can correlate the seismic even with changing mineral concentrations and identify the portion(s) of the river or tributaries that are closest to the released minerals. In another example, where a rainfall event causes increased erosion in a particular portion of the drainage basin, the machine learning model can observe changing mineral characteristics of the water to identify the mineralogy of the recently eroded portion of the drainage basin.

In example implementations, the machine learning model provides one or more "areas of interest" based on its received data. Those areas of interest can then be further interrogated, for example, with a hyperspectral scan, or other relatively high sensitivity or high intensity processes. In this manner, the machine learning algorithm can be used to efficiently allocate search efforts within a drainage basin.

Figure 4:
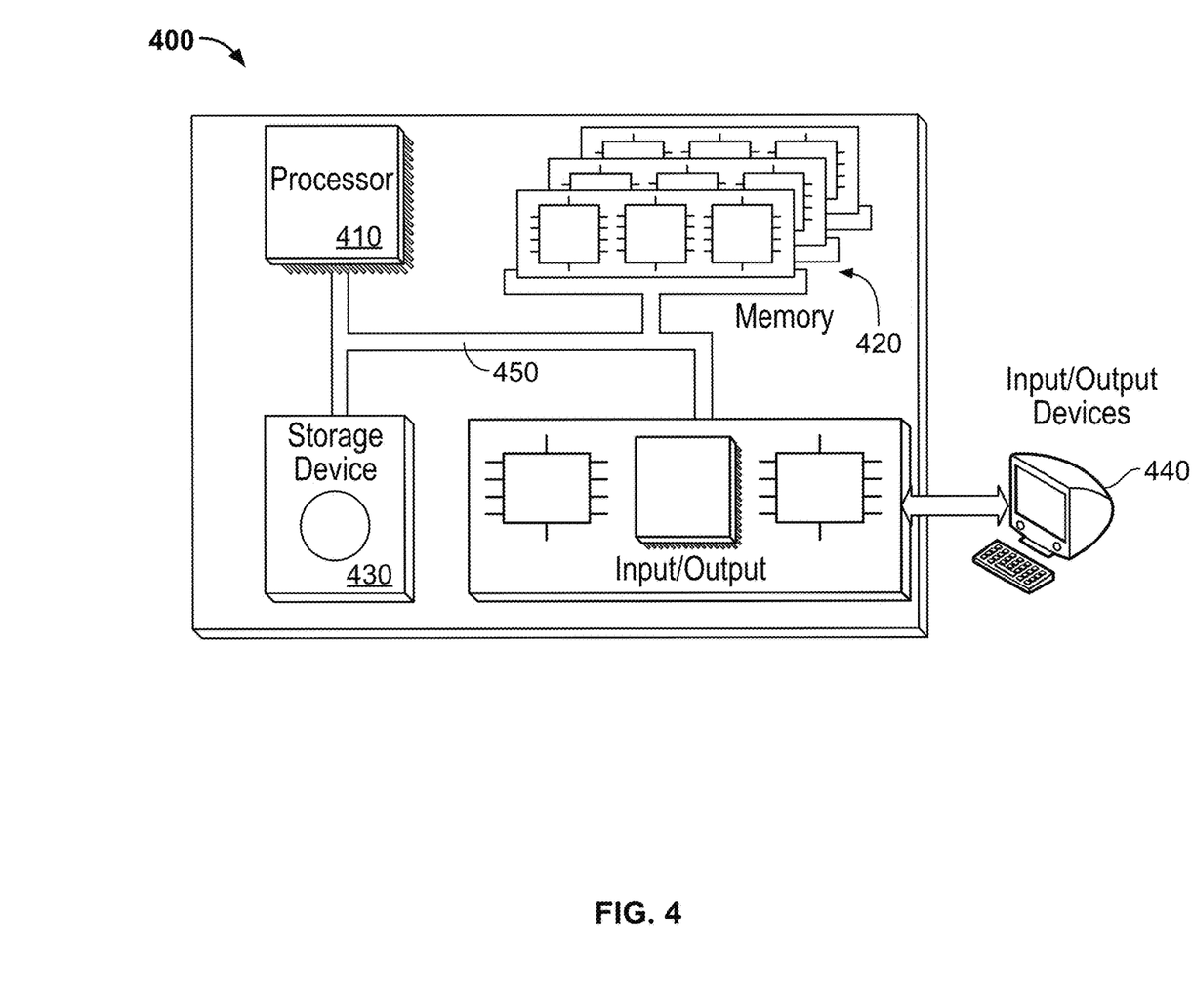
FIG. 4 is a schematic diagram of a computer system for performing operations according to the present disclosure.

FIG. 4 is a schematic diagram of a computer system 400. The system 400 can be used to carry out the operations described in association with any of the computer-implemented methods described previously, according to example implementations. In example implementations, computing systems and devices and the functional operations described in this specification can be implemented in digital electronic circuitry, in tangibly-embodied computer software or firmware, in computer hardware, including the structures disclosed in this specification and their structural equivalents, or in combinations of one or more of them. The system 400 is intended to include various forms of digital computers, such as laptops, desktops, workstations, servers, blade servers, mainframes, and other appropriate computers. The system 400 can also include mobile devices, such as personal digital assistants, cellular telephones, smartphones, and other similar computing devices. Additionally, the system can include portable storage media, such as Universal Serial Bus (USB) flash drives. For example, the USB flash drives may store operating systems and other applications. The USB flash drives can include input/output components, such as a wireless transducer or USB connector that may be inserted into a USB port of another computing device.

The system 400 includes a processor 410, a memory 420, a storage device 430, and an input/output device 440. Each of the components 410, 420, 430, and 440 are interconnected using a system bus 450. The processor 410 is capable of processing instructions for execution within the system 400. The processor may be designed using any of a number of architectures. For example, the processor 410 may be a CISC (Complex Instruction Set Computers) processor, a RISC (Reduced Instruction Set Computer) processor, or a MISC (Minimal Instruction Set Computer) processor.

In one implementation, the processor 410 is a single-threaded processor. In another implementation, the processor 410 is a multi-threaded processor. The processor 410 is capable of processing instructions stored in the memory 420 or on the storage device 430 to display graphical information for a user interface on the input/output device 440.

The memory 420 stores information within the system 400. In one implementation, the memory 420 is a computer-readable medium. In one implementation, the memory 420 is a volatile memory unit. In another implementation, the memory 420 is a non-volatile memory unit.

The storage device 430 is capable of providing mass storage for the system 400. In one implementation, the storage device 430 is a computer-readable medium. In various different implementations, the storage device 430 may be a floppy disk device, a hard disk device, an optical disk device, or a tape device.

The input/output device 440 provides input/output operations for the system 400. In one implementation, the input/output device 440 includes a keyboard and/or pointing device. In another implementation, the input/output device 440 includes a display unit for displaying graphical user interfaces.

The features described can be implemented in digital electronic circuitry, or in computer hardware, firmware, software, or in combinations of them. The apparatus can be implemented in a computer program product tangibly embodied in an information carrier, e.g., in a machine-readable storage device for execution by a programmable processor; and method steps can be performed by a programmable processor executing a program of instructions to perform functions of the described implementations by operating on input data and generating output. The described features can be implemented advantageously in one or more computer programs that are executable on a programmable system, including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits). The machine learning model can run on Graphic Processing Units (GPUs) or custom machine learning inference accelerator hardware.

To provide for interaction with a user, the features can be implemented on a computer having a display device such as a CRT (cathode ray tube) or LCD (liquid crystal display) monitor for displaying information to the user and a keyboard and a pointing device, such as a mouse or a trackball by which the user can provide input to the computer. Additionally, such activities can be implemented via touchscreen flat-panel displays and other appropriate mechanisms.

The features can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include a local area network ("LAN"), a wide area network ("WAN"), peer-to-peer networks (having ad-hoc or static members), grid computing infrastructures, and the Internet.

The computer system can include clients and servers. A client and server are generally remote from each other and typically interact through a network, such as the described one. The relationship of client and server arises by virtue of computer programs running on the respective computers and having a client-server relationship to each other.

While this specification contains many specific implementation details, these should not be construed as limitations on the scope of any inventions or of what may be claimed, but rather as descriptions of features specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can, in some cases, be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

Thus, particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

The foregoing description is provided in the context of one or more particular implementations. Various modifications, alterations, and permutations of the disclosed implementations can be made without departing from scope of the disclosure. Thus, the present disclosure is not intended to be limited only to the described or illustrated implementations but is to be accorded the widest scope consistent with the principles and features disclosed herein.

What is claimed is:

1. A computer-implemented method for determining a mineralogy of a portion of a drainage basin, comprising:
   identifying, by one or more hardware processors, topography data associated with a drainage basin comprising at least one body of water;
   identifying, by the one or more hardware processors, weather data associated with the drainage basin;
   identifying, by the one or more hardware processors, first sensor data associated with a first water sensor in the drainage basin;
   identifying, by the one or more hardware processors, second sensor data associated with a second water sensor, the second water sensor located downstream of the first water sensor in the drainage basin;
   providing the first sensor data, second sensor data, topography data, and weather data as input to a machine learning algorithm;
   determining, by the machine learning algorithm, a mineralogy of a portion of the drainage basin; and
   executing, based on the determined mineralogy of the portion of the drainage basin, a hyperspectral scan of the portion of the drainage basin.

2. The computer-implemented method of claim 1, wherein the topography data comprises at least one of elevation data or slope data within the drainage basin.

3. The computer-implemented method of claim 1, wherein the weather data comprises at least one of temperature data, precipitation data, or wind data for a time period.

4. The computer-implemented method of claim 3, wherein the time period is a least one month in duration.

5. The computer-implemented method of claim 1, wherein the first water sensor and the second water sensor are configured to measure a conductivity of the water.

6. The computer-implemented method of claim 1, wherein the first water sensor and the second water sensor are configured to measure at least one of:
   a mineral composition of the water;
   a flowrate of the water;
   a pH of the water; or
   a temperature of the water.

7. The computer-implemented method of claim 1, comprising:
  identifying, by the one or more hardware processors, remote sensing data associated with the drainage basin; and
  providing, by the one or more hardware processors, the remote sensing data as additional input to the machine learning algorithm.

8. The computer-implemented method of claim 7, wherein the remote sensing data comprises at least one of satellite imaging or synthetic aperture radar imaging.

9. The computer-implemented method of claim 1, comprising determining, by the machine learning algorithm, a recommended location for performing a hyperspectral scan in the drainage basin in response to determining the mineralogy of the portion of the drainage basin.

10. The computer-implemented method of claim 1, wherein the first water sensor is installed at a first location in the drainage basin and the second water sensor is located downstream of the first water sensor at a second location in the drainage basin.

11. The computer-implemented method of claim 10, comprising generating, by the machine learning algorithm and based on the determined mineralogy of the portion of the drainage basin, a third location in the drainage basin for deployment of a third sensor.

12. The computer-implemented method of claim 1, comprising generating, by the machine learning algorithm and based on the determined mineralogy of the portion of the drainage basin, a geographic search location for a particular mineral deposit within the portion of the drainage basin.

13. An apparatus comprising a non-transitory computer readable storage medium storing instructions that, when executed by at least one processor, cause the at least one processor to perform operations comprising:
  identifying topography data associated with a drainage basin comprising at least one body of water;
  identifying weather data associated with the drainage basin;
  identifying first sensor data associated with a first water sensor installed in the drainage basin;
  identifying second sensor data associated with a second water sensor, the second water sensor located downstream of the first water sensor in the drainage basin;
  providing the first sensor data, second sensor data, topography data, and weather data as input to a machine learning algorithm;
  determining, by the machine learning algorithm, a mineralogy of a portion of the drainage basin; and
  executing, based on the determined mineralogy of the portion of the drainage basin, a hyperspectral scan of the portion of the drainage basin.

14. The apparatus of claim 13, wherein the topography data comprises at least one of elevation data or slope data within the drainage basin.

15. The apparatus of claim 13, wherein the weather data comprises at least one of temperature data, precipitation data, or wind data for a time period.

16. The apparatus of claim 15, wherein the time period is a least one month in duration.

17. The apparatus of claim 13, wherein the first water sensor and the second water sensor are configured to measure a conductivity of the water.

18. The apparatus of claim 13, wherein the first water sensor and the second water sensor are configured to measure at least one of:
  a mineral composition of the water;
  a flowrate of the water;
  a pH of the water; or
  a temperature of the water.

19. The apparatus of claim 13, wherein the operations comprise:
  identifying remote sensing data associated with the drainage basin; and
  providing the remote sensing data as additional input to the machine learning algorithm.

20. The apparatus of claim 19, wherein the remote sensing data comprises at least one of satellite imaging or synthetic aperture radar imaging.

21. The apparatus of claim 13, wherein the operations comprise determining, by the machine learning algorithm, a recommended location for performing a hyperspectral scan in the drainage basin in response to determining the mineralogy of the portion of the drainage basin.

22. The apparatus of claim 13, wherein the first water sensor is installed at a first location in the drainage basin and the second water sensor is located downstream of the first water sensor at a second location in the drainage basin.

23. The apparatus of claim 22, wherein the operations comprise generating, by the machine learning algorithm and based on the determined mineralogy of the portion of the drainage basin, a third location in the drainage basin for deployment of a third sensor.

24. The apparatus of claim 13, wherein the operations comprise generating, by the machine learning algorithm and based on the determined mineralogy of the portion of the drainage basin, a geographic search location for a particular mineral deposit within the portion of the drainage basin.

25. A system, comprising:
  one or more processors;
  one or more tangible, non-transitory media operably connectable to the one or more processors and storing instructions that, when executed, cause the one or more processors to perform operations comprising:
    identifying topography data associated with a drainage basin comprising at least one body of water;
    identifying weather data associated with the drainage basin;
    identifying first sensor data associated with a first water sensor in the drainage basin;
    identifying second sensor data associated with a second water sensor, the second water sensor located downstream of the first water sensor in the drainage basin;
    providing the first sensor data, second sensor data, topography data, and weather data as input to a machine learning algorithm;
    determining, by the machine learning algorithm, a mineralogy of a portion of the drainage basin; and
    executing, based on the determined mineralogy of the portion of the drainage basin, a hyperspectral scan of the portion of the drainage basin.

26. The system of claim 25, wherein the topography data comprises at least one of elevation data or slope data within the drainage basin.

27. The system of claim 25, wherein the weather data comprises at least one of temperature data, precipitation data, or wind data for a time period.

28. The system of claim 27, wherein the time period is a least one month in duration.

29. The system of claim 25, wherein the first water sensor and the second water sensor are configured to measure a conductivity of the water.

30. The system of claim 25, wherein the first water sensor and the second water sensor are configured to measure at least one of:
- a mineral composition of the water;
- a flowrate of the water;
- a pH of the water; or
- a temperature of the water.

31. The system of claim 25, wherein the operations comprise:
- identifying remote sensing data associated with the drainage basin; and
- providing the remote sensing data as additional input to the machine learning algorithm.

32. The system of claim 31, wherein the remote sensing data comprises at least one of satellite imaging or synthetic aperture radar imaging.

33. The system of claim 25, wherein the operations comprise determining, by the machine learning algorithm, a recommended location for performing a hyperspectral scan in the drainage basin in response to determining the mineralogy of the portion of the drainage basin.

34. The system of claim 25, wherein the first water sensor is installed at a first location in the drainage basin and the second water sensor is located downstream of the first water sensor at a second location in the drainage basin.

35. The system of claim 34, wherein the operations comprise generating, by the machine learning algorithm and based on the determined mineralogy of the portion of the drainage basin, a third location in the drainage basin for deployment of a third sensor.

36. The system of claim 25, wherein the operations comprise generating, by the machine learning algorithm and based on the determined mineralogy of the portion of the drainage basin, a geographic search location for a particular mineral deposit within the portion of the drainage basin.

* * * * *